United States Patent [19]

Newkome et al.

[11] Patent Number: 5,703,271

[45] Date of Patent: Dec. 30, 1997

[54] METHOD OF UTILIZING ISOCYANATE LINKAGE FOR FORMING MULTI-TIER CASCADE POLYMERS

[75] Inventors: George R. Newkome, Temple Terrace, Fla.; Claus Weis, Pfeffingen, Switzerland

[73] Assignee: University of South Florida, Tampa, Fla.

[21] Appl. No.: 626,395

[22] Filed: Apr. 2, 1996

[51] Int. Cl.$^6$ .................................................. C07C 69/34
[52] U.S. Cl. .......................... 560/190; 560/330; 560/355; 560/357
[58] Field of Search ................................ 560/190, 330, 560/357, 355

[56] References Cited

U.S. PATENT DOCUMENTS

| | | | |
|---|---|---|---|
| 4,829,099 | 5/1989 | Fuller et al. | 560/330 |
| 5,154,853 | 10/1992 | Newkome et al. | 252/311 |
| 5,206,410 | 4/1993 | Newkome et al. | 558/389 |

*Primary Examiner*—Rachel Gorr
*Attorney, Agent, or Firm*—Kohn & Associates

[57] ABSTRACT

A method of synthesizing multitier cascade polymers and the polymers made thereby are formed by reacting at least one tier of a polymer with a functionalized isocyanate having the following formula:

$$O=C=N-C(CH_2-R)_3$$

with R being selected from the group including:

$$-(CH_2)_n-CH_2-COOR' \quad \text{a)}$$

with R' being selected from the group consisting of alkyl, cycloalkyl, aryl, heteroaryl- polycycloalkyl, adamantyl, n=0–10;

$$-O-(CH_2)_n-CH_2-COOR'$$

$$-O-(CH_2)_n-CH_2-CN \quad \text{b)}$$

with R' being selected from the group consisting of alkyl (c-1 to C(20), cycloalkyl (C-3 to C-10), aryl heteroaryl, polycycloalkyl, adamantyl, n=0–10; and $$-CH_2-(CH_2)_n-O-R'' \quad \text{c)}$$

with n=0–10, R" being selected from the group consisting of alkyl, cycloalkyl, aryl heteroaryl ester functionality, and a sulphur or a silicon atom bearing substituents selected from the group including:

$$-\overset{O}{\underset{\|}{C}}-X, \quad -\overset{S}{\underset{\|}{C}}-X, \quad -SO_2-R''', \quad -SiR_3$$

$$-CH_2-CH_2-CN, \quad -CH_2-CH_2-COOR'''$$

wherein R''' is alkyl (C-1 to C-20), cycloalkyl (C-3–C-10), aryl, heteroaryl, polycycloalkyl, adamantyl.

1 Claim, 3 Drawing Sheets

AMINO POLYMERS

METHOD OF UTILIZING ISOCYANATE LINKAGE FOR FORMING MULTI-TIER CASCADE POLYMERS

TECHNICAL FIELD

The present invention relates to highly branched molecules possessing a predetermined three dimensional morphology. More specifically, the present invention relates to micelles having uses in areas such as detergents, radioimaging, binding sites for drug delivery, polyfunctional basis and other areas of use.

BACKGROUND OF THE INVENTION

The art of methods of making and methods of using cascade polymers capable of forming unimolecular micelles is continuously growing. Unimolecular micelles are high molecular weight, highly branched, multifunctional molecules possessing a predetermined three dimensional morphology, as discussed in the U.S. Pat. No. 5,154,853 to applicants. As stated in the aforementioned '853 patent, synthetic strategies employed for the manufacture of such cascade polymers require consideration of factors such as the content of the initial core, the building blocks or monomers used as repeating units to produce tiers about the initial core, spacer molecules, branching numbers, dense packing limits, desired porosity of the molecule, guest molecules capable of insertion into the molecule, interreaction between the (uni)molecular micelles, as well as other factors. The critical factors in such synthesis remain the selection of the appropriate monomers or building blocks, governed by the type of branching desired.

The aforementioned '853 patent discloses a method of synthesizing unimolecular micelles using building blocks as disclosed in the U.S. Pat. Nos. 5,154,853 and 5,206,410, both to applicants. Generally, the methods of making cascade polymers as disclosed in the '853 patent include the steps of alkylating the branches of a multibranch core alkyl compound with a terminal alkyne building block including multiple ethereal side chains and then simultaneously reducing the alkyne triple bonds and deprotecting to form a multi-hydroxyl terminated multi-branched all alkyl polymer. This method a unimolecular micelle consisting essentially of a carbon core atom and essentially all alkyl arms extending therefrom.

The synthesis of the building blocks are disclosed in detail in the aforementioned '410 patent. Briefly, nitromethane and three equivalents of acrylonitrile are reacted under basic conditions to provide a nitroalkylnitrile. The nitrile is hydrolyzed under acidic conditions to give the corresponding tricarboxylic acid. The tricarboxylic acid is then reduced with diborane to the nitroalkyltriol. The nitro group of the triol is reduced with hydrogen and nickel to give the aminoalkyltriol "bis-homotris". An alternative protection route is provided by reacting the nitroalkytriol with 4-chlorobenzyl chloride to protect the hydroxyl groups by conversion of the triol to the triether. The triether is then reacted with acrylonitrile to give the corresponding beta-cyanoethyl triether. The cyanotriether is then reduced with diborane to give the amino triether. Finally, the amino triether is reduced with hydrogen and palladium to give the aminoalkyltriol "extended bis-homotris".

Alternatively, nitromethane and three equivalents of alkyl acrylate are reacted under basic conditions to provide the corresponding nitro trisalkylester. Alkaline hydrolysis furnishes the nitro-triscarboxylic acid. The nitro-triscarboxylic acid is then reduced with diborane or with lithium aluminum hydride to yield nitro-tris-3-hydroxyalkane. Suitable protection of the hydroxy functionalities with acyl chlorides, or substituted derivatives thereof or with chlorotrialkylsilanes provided high yields of hydroxy—protected nitro-triol which could be reduced to the corresponding amino-trialkoxysilane serving as convenient starting material for the preparation of a tert. isocyanate, as exemplified below.

Similarly, tris(hydroxymethyl)aminomethane may be reacted with acrylonitrile or with esters of acrylic acid to give tris[(cyanoethoxy)methyl]aminomethane and tris[(cyanoalkoxy)methyl]aminomethane, respectively.

It would be advantageous to provide a route of synthesis requiring less steps than the aforementioned prior art method. Also, the aforementioned synthesis requires an amine for reaction with acid. It would be also desirable to provide a universal reactive group monomer which could react with various other reactive groups affording flexibility in the synthetic routes and thereby providing expanded utility of the invention.

SUMMARY OF THE INVENTION

In accordance with the present invention, there are provided methods for synthesizing cascade molecules by reacting at least one tier of a functionalized structure with compounds of the type:

$$O=C=N-C(CH_2R)_3$$

with R being selected from the group including

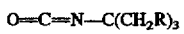

a)

with n=0–10; R' being selected from the group consisting of alkyl, cycloalkyl, aryl, heteroaryl, polycycloalkyl, adamantyl;

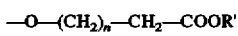

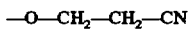

b)

with R' being selected from the group consisting of alkyl (C-1 to C-20), cycloalkyl (C-3 to C-10), aryl, heteroaryl, polycycloalkyl, adamantyl, wherein n=0–10;

c)

with n=0–10, R" being selected from the group consisting of alkyl, cycloalkyl, aryl, heteroaryl, ester functionality, and a sulphur or a silicon atom bearing substituents selected from the group including:

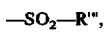

$-SiR_3'''$

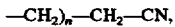

wherein R''' is alkyl (C-1 to C-20) cycloalkyl (C-3–C-10), aryl, heteroaryl, polycycloalkyl, adamantyl, n=0–10.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
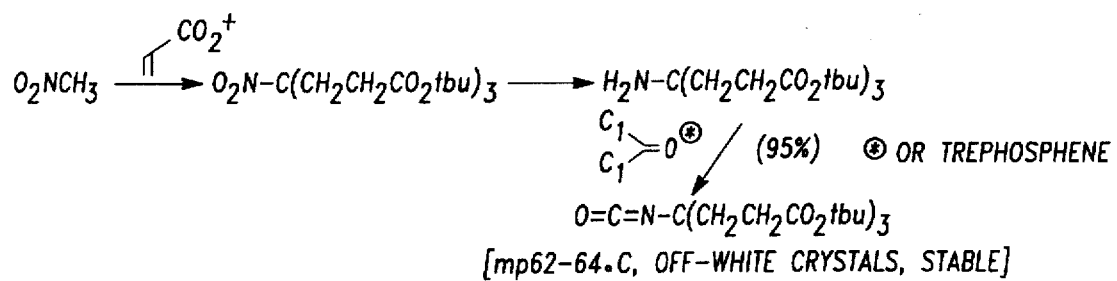
FIG. 1 is a schematic representation of a synthesis of the monomers made in accordance with the present invention.

Generally, the present invention provides a method of synthesizing cascade molecules and cascade polymers per se synthesized thereby. The method includes the general steps of reacting at least one tier of the cascade polymer with t-butyl isocyanate compound of the formula O=C=N—C(CH$_2$CH$_2$CO$_2$tbu)$_3$.

More specifically, referring to cascade molecules or polymers made in accordance with the present invention, such cascade molecules can be used to provide a (uni)molecular micelle including internal void areas, the void areas including reactive sites capable of covalent and noncovalent bonding to guest(s). Such (uni)molecular micelles made in accordance with the present invention are cascade structures which act as micelles. Such (uni)molecular micelles can be generally in the form of those disclosed in U.S. Pat. No. 5,154,853 to applicants, cited above, except to the extent they are modified in accordance with the present invention. Such molecules are essentially all alkyl molecules, or in the form of those disclosed in the Tomalia patents discussed above having a nitrogen core or branching site. Such compounds have predefined branching, depending upon the number of sequential "tier" additions that are performed in accordance with the above cited references. That is, the synthetic process is a matter of assembling the molecule in tiers or layers in accordance with the inventive method described herein.

The etymology of the term "Micelle", as employed in the classical or usual sense refers to a noncovalently associated collection (aggregate) of many simple molecules functioning as a unit having unique properties (for example, aqueous solublization of water in soluble materials) that are not observed with the individual molecules which comprise the micelle. Whereas, as used herein, (uni)molecular micelle or MICELLANE™ refers to a single macromolecule, possessing a covalently constructed superstructure, that can perform the same function or functions as a classical micelle.

An addition to these terms denote the incorporation of specific types of metals or nonmetals within the chemically accessible lipophilic interior of the unimolecular micelle.

Most generally, micelles or cascade polymers made in accordance with the present invention can be described as having at least one core atom, preferably a carbon atom, and arms branching from the core atom. In the syntheses of cascade polymers, cascade refers to the tiering or layerwise addition of monomers or "building blocks" that eventually comprise the resulting unimolecular micelle. These monomers or building blocks instill (1) a primary structure attributed to nuclei-connectivity, (2) a secondary structure attributed to fundamental nuclei interaction such as hydrogen binding, dipole interactions, and London forces, (3) a tertiary structure that can assume molecular shapes such as ribbons, zippers, threads, and spheres which are internal and external conformations induced by a secondary structure, and (4) a dynamic, structured void domain or "quasi-tertiary" structure of the unimolecular micelle determined by the combination of the primary, secondary and tertiary structures. A quasi-tertiary domain comprises one of the major domains of the micellar macromolecular structure which includes the immediate region above the micellar surface, the micellar per se and the micellar framework. All of these domains are active in that they can be used to effect chemical and physical changes of the (uni)molecular micelle, its environment, a molecular guest or guests, or any of the cited combinations.

This structure provides for the various utilities of micelles, as carriers of metals and the like, drugs or other guests allowing the micelles to be a drug delivery system or delivery system of other chemicals or the like in vivo and/or in vitro. For example, such micelles can carry toxins to be delivered to contaminants in a liquid environment, can be used as a drug delivery system for animals, including humans, can be used to remove materials from a system, such as contaminants from a detergent or the like, and many other uses that have been documented in the aforementioned patents as well as related patents in articles on the subject.

Termination of the arms of the micelles, or with larger branching, possibly midportions of the arms, may fold to form an outer surface of the micelle or cascade structure. The surface of the micelle is exposed to the immediately surrounding environment in which the micelle is disposed. This environment will have a certain hydrodynamic character, determined by properties such as pH, lipophilicity-hydrophilicity characteristics. Such surface characteristics also lead to general solubility of the micelle, even when carrying a relatively insoluble guest therein. Such surfaces can be readily coated with metal ions.

As discussed in the background art section, the aforementioned U.S. Pat. Nos. 5,136,096 and 5,206,410, as well as other publications, disclose a multi-step synthetic route beginning with the preparation of monomer building blocks and proceeding to the tier or cascade process. The present invention provides a more simplified and efficient method of building cascade molecules and/or polymers. Additionally, the present invention provides what can be considered universally effective building blocks in that the prior art amine requiring synthesis relied on amine terminations reacting with acids. The monomers of the present invention are much more highly reactive and therefore can be used more flexibly in synthetic reactions with terminal groups other than and including acids.

Most generally with regard to the subject method, the present invention provides a method of synthesizing multi-tier cascade polymers and the polymers made thereby. The polymers are formed by reacting at least one tier of a polymer with a functionalized isocyanate having the following formula:

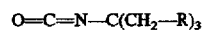

with R being selected from the group including:

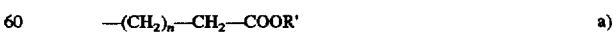

with n=0–10, R' being selected from the group consisting of alkyl, cycloalkyl, aryl, heteroaryl-polycycloalkyl, adamantyl;

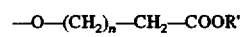

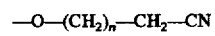

with n=0–10, R' being selected from the group consisting of alkyl (C-1 to C-20), cycloalkyl (C-3 to C-10), aryl heteroaryl, polycycloalkyl, adamantyl;

    c)

with n=0–10, R" being selected from the group consisting of alkyl, cycloalkyl, aryl heteroaryl ester functionality, and a sulphur or a silicon atom bearing substituents selected from the group including:

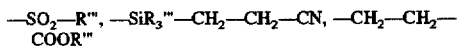

wherein R''' is alkyl (C-1 to C-20) cycloalkyl (C-3 to C-10), aryl, heteroaryl, polycycloalkyl, adamantyl. Specific examples of the aforementioned R groups are

---

R = CH$_2$CH$_2$CO$_2$R'
OCH$_2$CH$_2$CO$_2$R'
OCH$_2$CH$_2$CN
OCH$_2$CH$_2$CH$_2$OR"
OCH$_2$CH$_2$CH$_2$NR'R'''
OCH$_2$CH$_2$CH$_2$SR"
OCH$_2$CO$_2$R'
CH$_2$CH$_2$NR'$_2$
CH$_2$CH$_2$SR'

---

Referring more specifically to the inventive reaction, FIG. 1 exemplifies the general synthetic route to obtain the tert.-butyl isocyanate compound or tert.-structural analogs thereof.

The synthesis provides a high yield (approx. 95%) of off-white crystals, which are stable over a wide temperature range having a melting point of between 62°–64° C. The tert.-butyl isocyanate as well as the aforementioned structural analogs, as discussed and demonstrated below can be effectively and efficiently used in the synthesis of simple or multitier cascading structures. The conversion of the amine to the functionalized tert.-alkylisocyanate can be performed with phosgene, trichloromethylchloroformate (phosgene-dimer) or with bis(trichloromethyl)carbonate (phosgene-trimer) both of which are commonly use as potential substitutes for phosgene to avoid the severe hazards in laboratory use because of its volatility and high toxicity.

Figure 2:
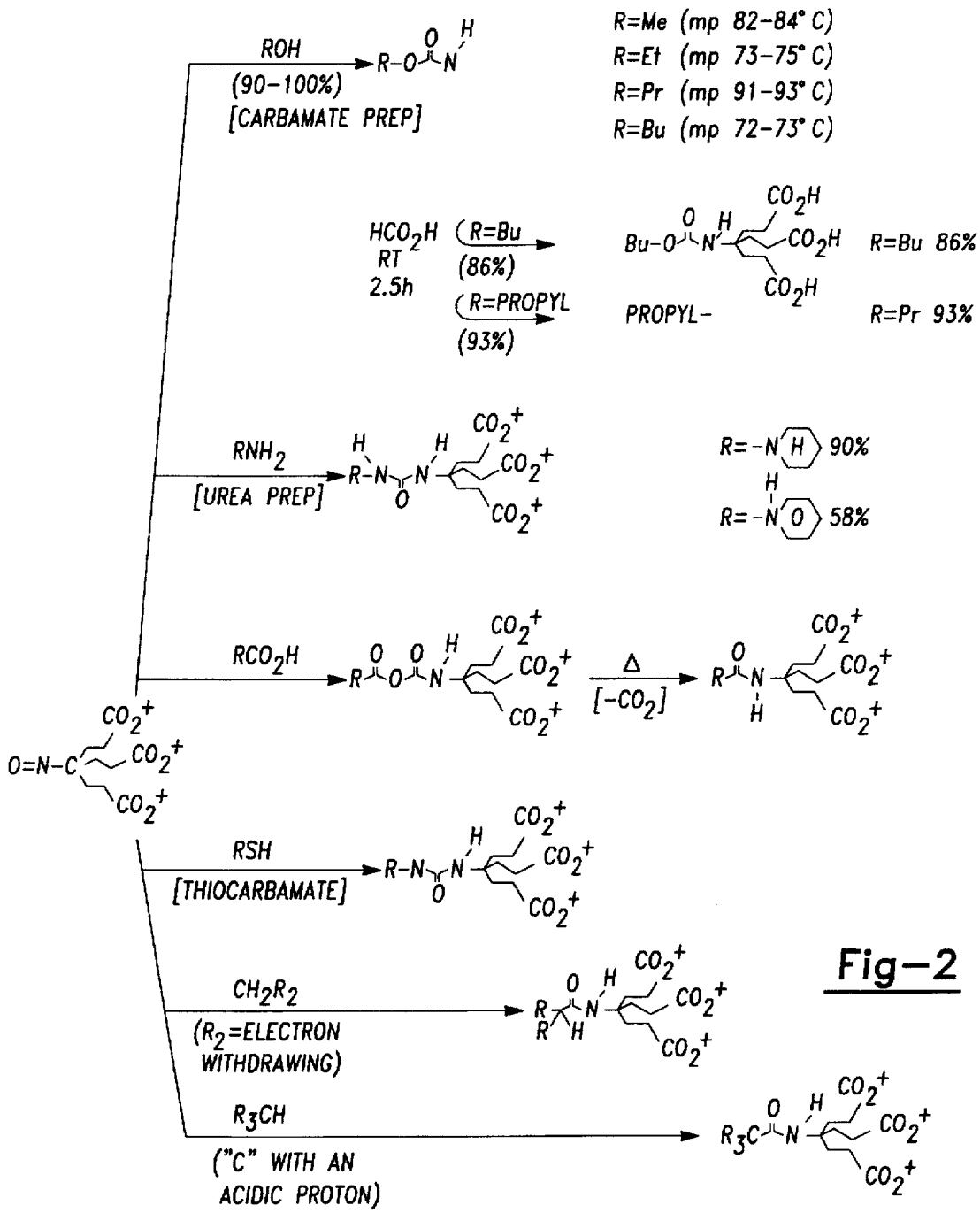
FIG. 2 is a schematic representation of a various synthesis demonstrating the flexibility of the reactivity of the monomers made in accordance with the present invention.

FIG. 2 shows the wide range of terminal groups reactive with the isocyanate monomer of the present invention. Hence, a tier of the cascade structure (or molecule) reacting with isocyanate portion of the t-butyl compound can include reactive groups selected from the group consisting of ROH, RNH$_2$, RCOOH, RSH, (CH$_2$)$_n$ R$_2$, and R$_3$CH where R is C-1 to C-10 and n=1–20. The reaction may be conducted at elevated temperatures varying from 50°–200° C. The preferred temperature range is 90°–100° C. Reaction times may vary from 1–60 hours depending on structural variations. The preferred reaction time is 20–24 hours at the preferred temperature range given above.

Solvents for the phosgenation of amines must be inert towards the amine, the isocyanate, the carbamidester chloride and hydrogen chloride. Furthermore, the boiling point should be substantially different from the isocyanate formed, so that a distillation separation appears feasible.

Solvents for this purpose are hexane, heptane, octane, benzene, toulene, xylenes, chloroform, dichloromethane, carbon tetrachloride, tetrachloroethane, ethyl acetate, dimethoxyethane, 2-butanone, acetonitrile, and nitrobenzene.

Organic bases suitable for the reaction include triethylamine, diisopropylethylamine, tripropylamine, or N,N-dimethylaminobenzene, DMAP, and related organic amines.

The reaction may also be carried out in a two-phase system: instead of a organic base, an aqueous solution of an alkali hydroxide, alkali bicarbonate or alkali carbonate can be use, as exemplified in the experimental section of this application.

The isocyanates can be isolated by distillation of the solvent, and subsequent crystallization from an inert solvent such as petrolem ether, pentane or hexanes. Further methods of purification include high vacuum distillation or column chromatography on silica or on basic or neutral aluminum oxide using inert solvents as listed above for the phosgenation reaction as eluents.

Further transformations of the tert-butyl isocyanate may be performed in an excess of the reaction partner. Such reactions may be carried out in the molten state of the two components and solvents used should be inert towards the isocyanate. Preferred solvents are toluene, xylenes, dimethylformamide.

As further demonstrated in FIG. 2, the reaction can be conducted under acid conditions forming carboxylic groups of the formula

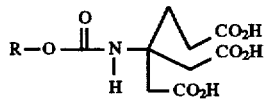

wherein R is the instilled structure or superstructure.

In view of the above, the variety of functional groups capable of reacting with the trifunctionalized isocyanate as set forth above allows great flexibility in adding tiers of the inventive monomers to various substrates. Hence, (uni) molecular micelles can be initiated and subsequently tiered upon substrates not previously acceptable or accessible to such synthesis.

For example, the reactive groups can be repeating units R on a polymer chain wherein the method of synthesis would include the step of reacting the t-butyl isocyanate compound set forth above with R groups of the polymer chain and forming a polymer chain with repeating groups

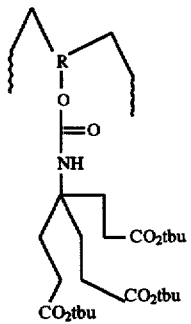

Thus produced is a core molecule upon which further tiers can be layered thereby having a substrate surface including (uni)molecular micelles covalently adhered thereto. Such substrates can be used as a protective coating wherein the micelles either absorb elements which would be otherwise contaminating from the environment of the substrate and isolate them within the micelles, or the micelles could be capable of releasing agents, such as decontaminating enzymes, chemicals or the like to rid a substrate surface of contamination. The surface modification by the addition of one or more tiers provides a hydrophilic canopy under which chemical inclusion, encapsulation and/or reactions can occur. The simple separation of diverse organic materials, such as drugs and physical resolution of molecular enantiomers will be possible. (Manning, et al. *J. Chem. Soc., Chem. Commun.* pp. 2139–2140 (1994)).

Figure 3:
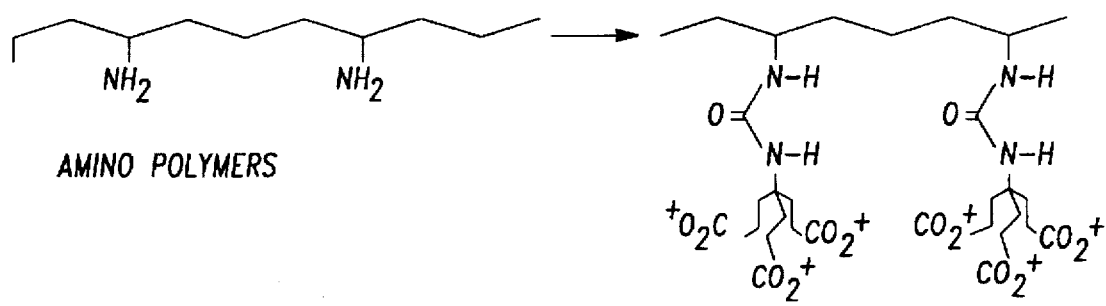
FIG. 3 is a schematic representation of a synthesis utilizing the inventive polymers of the present invention reacting with amine groups on a polymer surface.

A specific example of a polymer coating of micelle monomer cores over a polymer surface is shown in FIG. 3. Specifically, an amino polymer is shown wherein the monomers of the present invention are reacted therewith.

The attachment of 1→3 building blocks can be demonstrated by the reaction of poly(alkylamine) with the tert-butyl isocyanate, as well as oxygenated counterparts, to generate the coating of the polymeric backbone with multiple cascade centers. Subsequent hydrolysis of the multiple cascade center afforded new multiple hydrophilic units, which instill a water soluble canopy to the polymeric material. The canopy can be extended by subsequent treatment with the polyfunctionalized isocyanate monomer.

Figure 4:
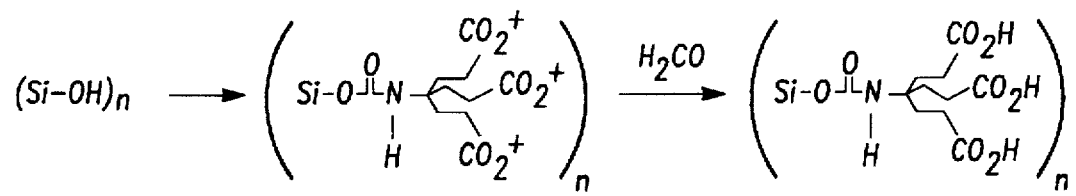
FIG. 4 is a schematic representation of the reaction of the monomers of the present invention on the surface of a silicon bead.

Such flexibility of reaction can also extend to various chemical surfaces, such as a siloxane surface of silicon beads. FIG. 4 shows a schematic representation of a reaction of monomers made in accordance with the present invention with the surface of a silicon bead. More specifically, the reactive groups on the surface are (SiOH) on a silica bead. The method includes the steps of reacting the t-butyl compound of the present invention with the (SiOH) groups to form a product having groups of the formula

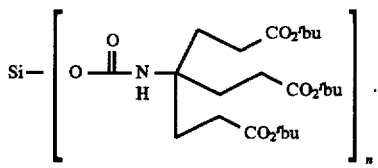

Hence, beads can be constructed having a plurality of micelles on the surface thereof. Such micelles can be used in various processes, such as column chromatography or the like for the selective removal of agents from the material flowing through the column or addition thereto.

Figure 5:
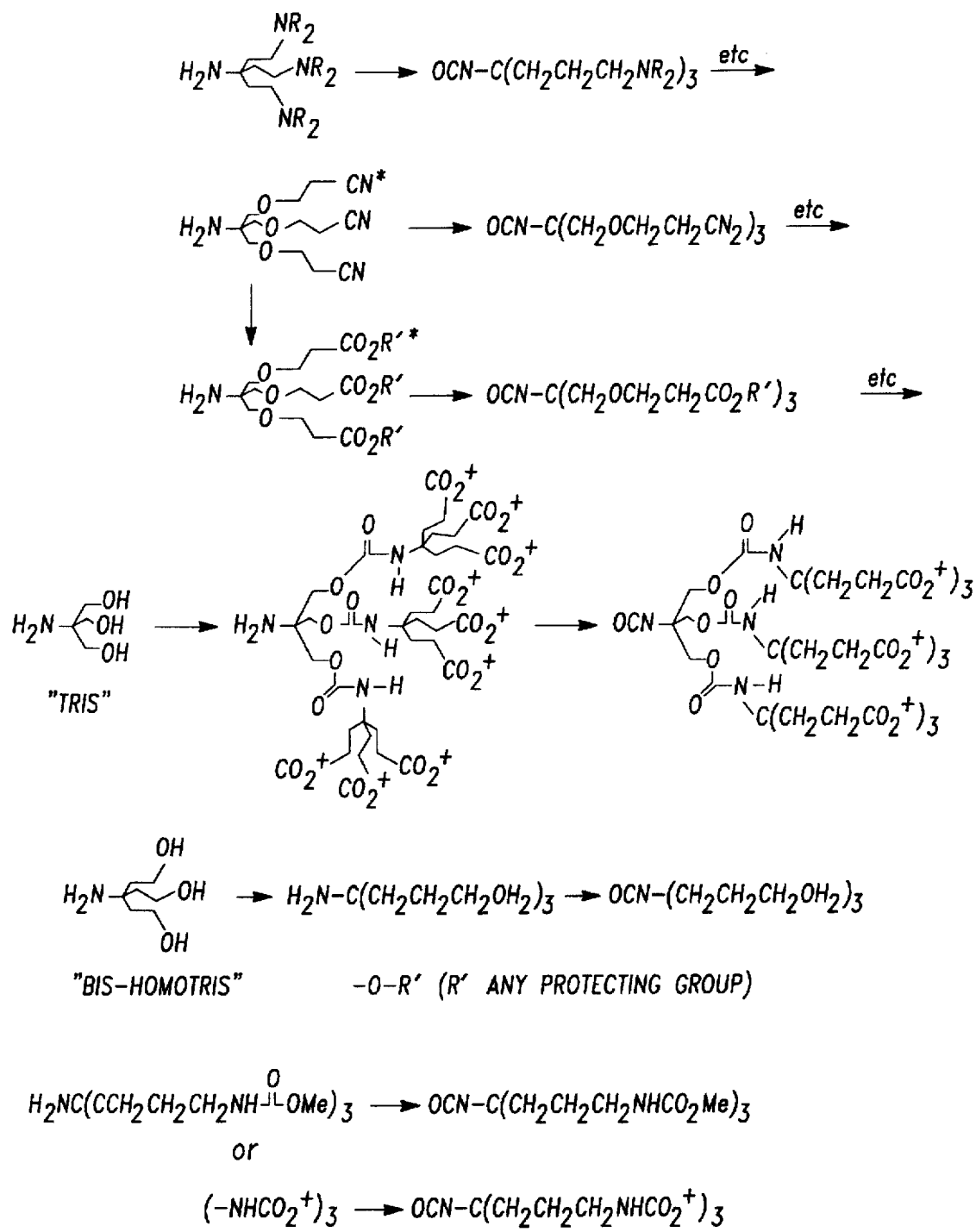
FIG. 5 is a schematic representation of several monomers reacting with the present invention.

In view of the above, the present invention provides several novel stable monomers capable of a wide variety of synthesis. For example, FIG. 5 shows several monomers disclosed by applicants in the above patents which can be utilized in accordance with the present invention resulting is the highly reactive isocyanate monomers. Thus, as shown in FIG. 5, with regard to the tris monomer, micellar structures can be formed utilizing tris and bis homotris monomers (the bis homotris monomer requiring protecting groups R' such as those well known in the art to construct construct cascade polymers including the

linkage. Hence, cascade molecules and/or polymers having the formula

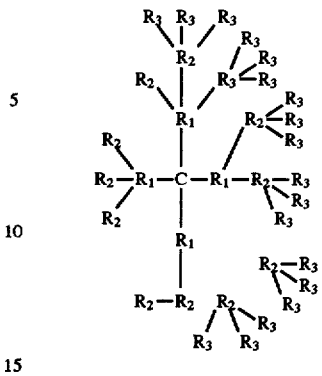

wherein $R_1$ is an alkyl having C3 to C20, $R_2$ is an alkyl having C3 to C20, $R_3$ is selected from the group consisting of H, alkyl, alkaryl, aryl, ammonium, sulfonium, phosphonium, and metal salts, each of $R_1$, $R_2$ and $R_3$, respectively, defining a tier about the central carbon atom, at least one of said tiers being bond to the next of said tiers through an

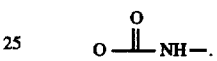

linkage.

In view of the above, most broadly, the invention provides a cascade polymer consisting essentially of a core atom, preferably carbon, and essentially all alkyl arms extending therefrom wherein the arms consist of a series of tiers. At least one of the tiers is bound to the

linkage.

Also, with regard to the monomer aspect of the present invention, most generally the present invention provides a stable trifunctionalized isocyanate. It is thermally stable and its reactivity is controllable.

The following examples demonstrate the synthesis of cascade polymers in accordance with the present invention. Also, the examples demonstrate the ability to prepare diverse cascade structures in a single step from new trifunctionalized alkylisocyanates. The products are thermally stable and possess controllable reactivity.

Di-tert-butyl 4-isocyanato-4[2-(tert-butoxycarbonyl)ethyl]heptanedioate.

A solution of di-tert-butyl 4-amino-4-[2-(tert-butoxycarbonylethyl]heptanedioate (8.3 g, 0.02mol), triphosgene [bis(trichloromethyl)carbonate](4.0 g, 0.013 mol), and triethylamine (5g, 0.05 mol) in benzene (400 mL), was stirred and heated to gentle reflux for 2.5 hours. The white precipitate was filtered from the solution over a glass sintered funnel, and washed with benzene (80 mL). The filtrate was washed with 3% aqueous sodium hydroxide solution (50 mL), layers separated, and the organic phase dried with magnesium sulfate (10 g). Distillation of benzene yielded a light yellow oil which solidified on standing, to give crystals (8.4 g, 95% ) of product. Crystals were dissolved in petroleum ether (low boiling fraction 30°–50° C.) (45 mL), the solution filtered, and placed in a deep freezing compartment for 30 hours. Filtration yielded slightly off-white crystals ( 8.4 g, 95% ), mp. 62–64° C.; IR (KBr): 2262 (NCO), 1734 (COO), 1159 (C—O) cm$^{-1}$; $^1$H NMR (CDCl$_3$): 1.34 (s, CH$_3$, 27H); 1.74 (t, J=4.2, 6H); 2.18 (t, J=4.2 6H); $^{13}$C NMR (CDCl$_3$) 27.8 (CH$_3$), 33.89 (CH$_2$CO), 29.9 (C—CH$_2$CH$_2$—), 61.82 (C—N); 80.57 (C—CH$_3$), 122.18 (N=C=O), 171.68 (COO).

Phosgenation in 2-phase system.

To a solution of phosgene 12 g., 0.12 mol)in chloroform (300 mL) is added with stirring at 0°–5° C. over a period of thirty minutes, a solution of 44 g (0.1 mol) of di-tert.-butyl4-amino-4-[2-tert.-butoxycarbonyl)-ethyl]-heptanedioate in chloroform (100 mL) and simultaneously a solution of sodium hydroxide (9.6 g) dissolved in water (80 mL). The phases were separated after one hour, and the organic phase dried over sodium sulfate. Distillation of the solvent yielded product (43 g, 92%) as off-white crystals, mp 62° C.

Phosgene (6 g, 0.06 mol) was slowly introduced at 0.5° C. into a stirred solution of amine (22 g, 0.1 mol) in methylene chloride (500 mL) and triethylamine (6 g, 0.06 mol). The suspension was stirred at ambient temperature for two hours. Triethylamine was filtered from the solution and the work-up performed as reported under 1), yield of isocyanate: 25 g (85%).

Alkylurethanes of di-tert-butyl 4 isocyanate4-[tert-butoxycarbonyl)ethyl]heptanedioate.

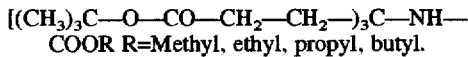
[(CH$_3$)$_3$C—O—CO—CH$_2$—CH$_2$—)$_3$C—NH—COOR R=Methyl, ethyl, propyl, butyl.

1) R=Methyl.

A solution of di-tert-butyl 4-isocyanato-4-[tert-butoxycarbonyl)ethyl]heptanedioate (0.44g, 0.001 mol) in methanol was refluxed for 20 hrs. Distillation of the solvent at reduced pressure yielded on oil, which solidified on standing, 430mg, (91%), mp 82–84° C. (petroleum ether); TLC: ethyl acetate/cyclohexane on SiO$_2$); $^1$H NMR (CDCl$_3$): δ1.43 (s, 27H, CH$_3$), 1.89 (t, J=7.3 Hz, 6H, CH$_2$), 29.69 (CO—CH$_2$), 51.23 (O—CH$_3$), 56.10 (C—NH), 80.13 [(CH$_3$)$_3$C], 154.64 (NH—CO), 172.26 (COO).

2) R =Ethyl

The reaction was performed as reported under example 1). Yield: 92%, top. 73°–75° C. (petroleum ether); $^1$H NMR (CDCl$_3$): δ1.20 (t, J=7.0 Hz,CH$_3$, 3H), 1.42 (s, CH$_3$, 27H), 1.88 (t, J=7.3 Hz, 6H, CH$_2$), 2.20 (t, J=7.3 Hz, 6H, CH$_2$) 4.03 (q, CH$_2$, 2H), 4.66 (s, br, NH). $^{13}$C NMR (CDCl$_3$): δ14.42 (CH$_2$—CH$_3$), 27.96 [(CH$_3$)$_3$], 29.60 (CH$_2$—CH$_2$), 30.03 (CO—CH$_2$), 56.28 (C—NH), 62.40 (O—CH$_2$), 80.44 [(CH$_3$)$_3$C], 54.60 (CO—NH), 172.46 (COO).

3) R=Propyl.

The reaction was performed as reported under example 1). Yield: 86%; top. 91°–93° C. (petroleum ether); $^1$H NMR (CDCl$_3$): δ0.90 (t, J=7Hz, 3H, CH$_3$), 1.41 [s, 27H,(CH$_3$)$_3$], 1.63 (t, J=8Hz,2 H, CH$_2$), 1.87 (t, J=8Hz, 2 H, CH$_2$), 2.19 (t, J=8Hz, 2H, CH$_2$), 3.93 (t, J=7 Hz, 2H, OCH$_2$), 4.67 (br, NH); $^{13}$C NMR (CDCl$_3$): δ10.13 (CH$_3$), 22.12 (CH$_2$—CH$_3$), 27.87 [(CH$_3$)$_3$], 29.52 (CO—CH$_2$—CH$_2$), 29.96 (CO—CH$_2$—CH$_2$), 56.19 (C—NH), 65.76 (O—CH$_2$), 80.30 [(CH$_3$)$_3$C], 154.20 (NH—COO), 172.36 (COO).

4)R=Butyl

The reaction was performed as reported under example 1). Yield: 100%; mp. 72–73° C. (petroleum ether); δ1.02 (t, J=7.0Hz, 3H, CH$_3$), 1.43 [s, 27H,(CH$_3$)$_3$], 1.53–1.63 (m, CH$_2$—CH$_2$, 4H), 1.88 (t, J=7Hz, 6H, CH$_2$), 2.20 (t, J=7Hz, 6H, CH$_2$), 3.98 (t, 2H, CH$_2$—O), 4.68 (br, NH); $^{13}$C NMR (CDCl$_3$): δ13.62 (CH$_3$), 18.96 (CH$_3$—CH$_2$), 27.94 [(CH$_3$)$_3$], 29.58 (CO—CH$_2$—CH$_2$), 30.03 (CH$_3$—CH$_2$—CH$_2$), 30.90 (CO—CH$_2$—CH$_2$), 56.25 (C—NH), 64.14 (O—CH$_2$), 80.41 [(CH$_3$)$_3$C], 154.59 (NH—CO), 172.44 (COO).

4-(beta-Carboxyethyl)-4-N-butylcarbamoyl)-1,7-heptanedioic acid.

A solution of n-butylurethane (515 mg, 1 mmol) in formic acid was stirred for 2 hrs. then distilled in a rotating evaporator, toluene (15 mL) added, and again distilled in a vacuo. The procedure was repeated twice yielding a glassy product, which solidified on having it attached to a vacuum manifold overnight, yielding a non-crystalline, white material, mp 110°–112° C.; 300 mg (86%); $^1$H NMR (DMSO-d$_6$): δ0.86 (t, J=7Hz, 3H, CH$_3$), 1.22–1.51 (m, CH$_2$—CH$_2$, 4H), 1.74 (t, J=7Hz, 6H, CH$_2$), 2.09 (t, J=7Hz, 6H, CH$_2$), 3.87 (t, J=7Hz, 3H, CH$_3$), 6.70 (s, NH), 12.0 (br, COOH); $^{13}$C NMR(DMSO-d$_6$) δ13.90 (CH$_2$—CH$_2$—COOH), 31.07 (CH$_2$—CH$_2$—COOH), 55.91 (C—NH), 63.21 (O—CH$_2$), 154.88 (NH—CO), 174.72 (COO).

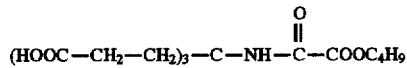
(HOOC—CH$_2$—CH$_2$)$_3$—C—NH—C—COOC$_4$H$_9$ 1,9-Dicyano-5-(2-oxa-4-cyanobutyl)-3,7-dioxanonyl-5-isocyanate.

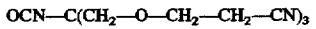
OCN—C(CH$_2$—O—CH$_2$—CH$_2$—CN)$_3$

Tricyanoamine was prepared essentially according to the procedure outlined by G. R. Newkome and X. Lin, (Macromolecules, 24:1443 (1991)).

To a solution of tricyanoamine (2.80 g, 0.01 mol) in methylenedichloride (100 mL) was added triethylamine (2.42 g, 3.33 mL, 24 mmol), followed by slow addition of triphosgene (1,176 g, 4 mmol). The solution came to near reflux and was stirred at ambient temperature for three hrs. Then the solvent was removed in vacuo. A mixture of ethyl acetate and ether (1:1) (150 mL) was added to the solid residue, and triethylamine hydrochloride was filtered. The filtrate was washed with dilute 2% aqueous sodium bicarbonate solution (2×30 mL), then water and dried (MgSO$_4$). Distillation of the solvent in vacuo furnished product, as a light yellow oil (2.90 g, 94%): $^1$H NMR(CDCl$_3$) δ2.64(t, J=6.0Hz, 6H, CH$_2$—CN), 3.60 (s, 6H, CH$_2$—O), 3.74 (t, J=2.5Hz, O—CH$_2$); $^{13}$C NMR(CDCl$_3$): δ126.85 (NCO), 117.62 (CN), 70.57 (CH$_2$—O), 65.68 (—O—CH$_2$—), 63.18 (C—NCO), 18.44 (CH$_2$—CN); IK(KBr): 2263 (NCO).

1,9-Dicyano-5-(2-oxa-4-cyanobutyl)-3,7-dioxanonyl-5-N-propyl carbamate.

(NC—CH$_2$—CH$_2$—O—CH$_2$—)$_3$C—NH—COOC$_3$H$_7$

The trifunctionalized isocyanate (0.6 g, 2 mmol) was dissolved in propanol (15 mL) and the solution refluxed for 20 hrs. Solvent was removed in vacuo yielding product as an oil (700 mg, 95.5%) which was purified on basic aluminum oxide [EtOAc, toluene(2:8) ]; $^1$H NMR(CDCl$_3$): δ0.92 (t, J=4Hz, 3H, CH$_3$), 1.62 (m, CH$_2$, 2H), 2.61 (t, J=6Hz, 6H, CH$_2$—CN), 3.76 (t, J=7Hz, CH$_2$—O, 6H), 3.78 (s, O—CH$_2$, 6H), 3.93 (t, J=7Hz, 2H, O—CH$_2$), 5.01 (br, NH); $^{13}$C NMR(CDCl$_3$): δ9.96 (CH$_3$), 18.50 (CH$_2$—CN), 21.88 (CH$_3$—CH$_2$), 58.26 (C—NH), 65.42 (NC,CH$_2$—CH$_2$—O), 65.87 (COO—CH$_2$), 68.88 (O—CH$_2$—), 117.73 (CN), 155.12 (NH—CO).

N-Acetyl-[1,9-dicyano-5-(2-oxa-4-cyanobutyl)-3,7 dioxanonylamine].

(NC—CH$_2$—CH$_2$—O—CH$_2$—)$_3$C—NH—CO—CH$_3$

A solution of 1,9-dicyano-5(2-oxa-4-cyanobutyl)-3,7-dioxanonyl-5-isocyanate (300 mg, 1 mmol) in acetic acid (8 mL) was refluxed for ten hrs. The excess acetic acid was distilled in vacuo. toluene (15 mL) was added and again concentrated in vacuo yielding a red oil (300 mg), which was purified on silica gel (EtOAc/-cyclohexane, 8:2) to furnish the product, as a light yellow oil (200 mg, 60%) $^1$H NMR(CDCl$_3$): δ1.99(s, 3H, CH$_3$), 2.61 (t, J=6Hz, 6H, CH$_2$—CN), 3.69 (t, J=6Hz, 6H, CH$_2$—O), 3.84 (s, 6H, O—CH$_2$), 5.73 (br, NH); $^{13}$C NMR (CDCl$_3$): δ18.41 (CH$_2$—CN), 23.75 (CH$_3$—CO), 59.38 (C—NH), 65.42 (CH$_2$—CH$_2$—CN), 68.53 (O—CH$_2$), 117.82 (CN), 170.64 (CO—NH).

N-Propionyl-[1,9-dicyano-5-(2-oxa-4-cyanobutyl)-3,7-dioxanonylamine].

A solution of the trifunctionalized isocyanate (500 mg, 16 mmol) in propionic acid (3 mL) was heated to 95°–100° C. for 48 hrs. The acid was neutralized with aqueous sodium bicarbonate, and product extracted with ethyl acetate (2×20 mL). The extract was dried (MgSO$_4$) and solvent removed in a vacuo yielding a dark colored oil, which was purified as described above yielding the product as an oil (320 mg, 59%); $^1$H NMR CDCl$_3$): δ1.11 (t, J=3Hz, 3H, CH$_3$), 2.21 (t/d, J=7Hz, 2H, CH$_2$), 2.62 (t, J=6Hz, 6H, CH$_2$—CN), 3.68 (t, J=6Hz, CH$_2$O, 6H), 3.84 (s, 6H, OCH$_2$), 5.70 (br, NH); $^{13}$C NMR(CDCl$_3$): δ9.24 (CH$_3$), 18.3 (CH$_2$—CN), 29.64 (CH$_2$—CH$_3$), 59.05 (C—NH), 65.26 (NC—CH$_2$—CH$_2$—O), 68.54 (O—CH$_2$), 117.71 (CN), 170.90 (CO).

N-Phenyl-N'-[1,9-Dicyano-5(2-oxa-4-cyanobutyl)-3,7-dioxanonyl]urea.

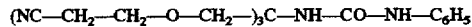

A solution of the trifunctionalized (500 mg, 16 mmol) in aniline (4 mL) was heated to 50° C. for 37 hrs. The solution was added to dilute HCl(50 mL) and the oil extracted with ethyl acetate (50 mL). The extract was washed with water (2×10 mL), and dried (Na$_2$SO$_4$). The solvent was removed in vacuo, and the remaining oil purified on basic aluminum oxide [EtOAc/toluene (9:1)], yielding product as an oil. After addition of 10 mL of ether, crystals separated which were filtered and recrystallized from methanol, mp 90°–92° C. $^1$H NMR (CDCl$_3$): 2.62 (t, J=6Hz, CH$_2$—CN), 3.72 (t, J=6Hz, 6H, CH$_2$—O), 3.88 (s, 6H, OCH$_2$), 5.21 (br, NH), 6.58 (br,NH), 7.29–7.30 (m, 5H, arom. H); $^{13}$C NMR (CDCl$_3$): 18.51 (CH$_2$—CN), 58.91 (C—NH), 65.53 (CH$_2$—CH$_2$—O), 69.43 (O—CH$_2$), 118.18 (CN), 119.47, 112.74, 129.00, 138.74 (arom. C), 154.89 (NH—CO—NH).

Reaction of (tris-hydromymethyl)aminomethane and di-tert.-butyl-4-isocyanato-4-[2-(tert.-butoxycarbonyl)ethylheptanedioate.

A solution of (tris-hydroxymethyl)aminomethane (1.2 g, 10 mmol) and the trifunctionalized isocyanate (4.4 g, 10 mmol) in DMF (20 mL) was heated to 90°–100° C. for 15 hrs. The solvent was removed in vacuo and the product purified by chromatography on silica gel [EtoAc/cyclohexane (2:8)]yielding a white, non-crystalline material mp 120°–124 ° C.

(6—Carbometyhoxy-2-oxabutyl)-4,8-dioxaundecane-6-isocyanato-1, 11-dicarboxylic acid dimethylester.

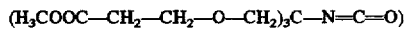

To a stirred solution of 6-amino-6,6-bis-(carbomethoxy-2-oxabutyl)-4,8-dioxaundecane-1, 11-dicarboxylic acid dimethylester (3.79 g, 0.01 mol) and triethylamine (2.20 g, 3.07 mL, 0.023 mol) in ether (80 mL) was added a solution of triphosgene (1.09 g, 0.00366 mol) in ether (25 mL) at a temperature of 10°–15° C. over a period of five minutes. Then the slurry was stirred for two hours at 25° C. Triethylamine hydrochloride was filtered from the solution and washed on the filter with ether (30 mL). The filtrate was washed with aqueous sodium carbonate solution (3%) (20 mL), followed by water (20 mL), and dried over magnesium sulfate. Distillation of the ether yielded the product, as an oil: (3 g, 75%); $^1$H NMR (CDCl$_3$): 2.55 (t, J=6.4Hz, 6H, CH$_2$—COO), 3.43 (s, 6H, CH$_2$—O), 3.67 (s, 9H, CH$_3$), 3.70 (t, J=6Hz, 6H, CH$_2$—CH$_2$—COO); $^{13}$C NMR (CDCl$_3$): 19.70 (CH$_2$—COO), 51.17 (OCH$_3$), 63.35 (=C—N—), 66.58 (O—CH$_2$—CH$_2$), 70.78 (CH$_2$—O), 126.78 (NCO), 171.35 (COO); IR(KBr): 2263 (NCO). Anal. Calcd for C$_{17}$H$_{27}$NO$_{10}$ (405.39): C, 50.36, H, 6, 71, N, 3.46, Found: C,50.45, H, 6.68, N. 3.51.

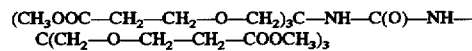

A solution of (6-amino-6-carbomethoxy-2-oxabutyl)-4,8-dioxaundecane-1, 11-dicarboxylic acid dimethylester (0.38 g, 0.001 mol) and (6-carbomethoxy-2-oxabutyl)-4,8-dioxaundencane-6-isocyanato-1, 11-dicarboxylic acid dimethylester (0.40 g, 0.001 mol) in toluene (30 mL) was heated to 65° C. for forty-eight hours. Solvent was distilled, and the residual oil chromatographed on basic aluminum oxide (50 g, eluted with ethyl acetate/Methanol 10:0.3), yielding 0.56 g (78%) of a viscous oil; $^1$H NMR (CHCl$_3$): 2.55 (t, J=6.3Hz, 12H, CH$_2$—COO), 3.65–3.72 (m, CH$_2$—O, CH$_2$—CH$_2$COO, 24H), 3.68 (s, 18H, CH$_3$); $^{13}$C NMR (CDCl$_3$): 34.68 (CH$_2$—COOCH$_3$), 51.47 (OCH$_3$), 58.77 (=C=NH), 66.68 (O—CH$_2$—CH$_2$—), 69.92 (O—CH$_2$), 157.00 (NHCONH), 171.97 (COO), Anal.Calcd for C$_{33}$H$_{56}$H$_2$O$_{19}$: C, 50.50; H, 7.19; N, 3.56; Found: C, 50.62; H, 7.11; N, 3.51.

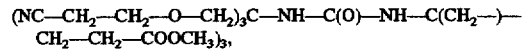

A solution of 5-amino-4-cyano-2-oxabutyl)-1,9-dicyano-3, 7-oxa-nonane (0.56 g, 0.002 mol) and (6-carbomethoxy-2-oxabutyl)-4,8-dioxaundecane-6-isocyanato-1, 11-dicarboxylic acid dimethylester (0.81 g, 0.002 mol) in toluene (5 mL) was heated to 65° C. for thirty-eight hours. Distillation of the solvent gave a viscous oil which after chromatography on basic aluminum oxide (ethyl acetate, methanol 10:0.3) yielded 1.01 g (73%) of product. $^1$H NMR (CDCl$_3$): 2.56–2.67 (m, CH$_2$—COO, CH$_2$—CN, 12H) 3.69 (s, 9H, CH$_3$), 3.67–3.79 (m, CH$_2$—O, CH$_2$—CH$_2$—COO, 24H), 5.11 (br, s, NH), 5.22 (br, s, NH); $^{13}$CNMR (CDCl$_3$): 18.66 (CH$_2$—CN), 34.61 (CH$_2$—COOCH$_3$), 51.52 (OCH$_3$), 58.77 (=C—NH, ester part), 58.84 (=C—NH), 65.73 (O—CH$_2$—CH$_2$—CN), 66.70 (O—CH$_2$—CH$_2$), 69.76 (O—CH$_2$), 69.91 (O—CH$_2$, ester part), 117.95 CN), 156.91 (NH—CO—NH), 172.07 (COO).

In view of the above, the present application provides a method of synthesizing cascade (macro)molecules, and/or polymers used to make the same. Such monomers and polymers can be used for various utilities demonstrated and discussed above.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. A t-butyl isocyanate monomer of the formula $$O=C=N-C(CH_2CH_2CO_2tbu)_3.$$

* * * * *